US011268967B2

(12) United States Patent
Chattopadhyay et al.

(10) Patent No.: US 11,268,967 B2
(45) Date of Patent: Mar. 8, 2022

(54) DEVICE FOR VISUAL DETECTION OF BILIRUBIN

(71) Applicant: INDIAN INSTITUTE OF TECHNOLOGY, GUWAHATI, Assam (IN)

(72) Inventors: Arun Chattopadhyay, Assam (IN); Anumita Paul, Assam (IN); Srestha Basu, Assam (IN); Amaresh Kumar Sahoo, Assam (IN)

(73) Assignee: INDIAN INSTITUTE OF TECHNOLOGY, GUWAHATI, Assam (IN)

( * ) Notice: Subject to any disclaimer, the term of this patent is extended or adjusted under 35 U.S.C. 154(b) by 452 days.

(21) Appl. No.: 15/572,779

(22) PCT Filed: Jun. 2, 2016

(86) PCT No.: PCT/IN2016/000140
§ 371 (c)(1),
(2) Date: Nov. 27, 2017

(87) PCT Pub. No.: WO2016/193996
PCT Pub. Date: Dec. 8, 2016

(65) Prior Publication Data
US 2018/0149663 A1 May 31, 2018

(30) Foreign Application Priority Data
Jun. 4, 2015 (IN) .......................... IN631/KOL/2015

(51) Int. Cl.
*G01N 33/72* (2006.01)
*A61B 5/1455* (2006.01)
(Continued)

(52) U.S. Cl.
CPC ......... *G01N 33/728* (2013.01); *A61B 5/1455* (2013.01); *A61B 5/14546* (2013.01);
(Continued)

(58) Field of Classification Search
CPC ............. G01N 33/728; G01N 21/6447; G01N 21/643; G01N 2021/6439;
(Continued)

(56) References Cited

U.S. PATENT DOCUMENTS

| 3,992,158 A | * | 11/1976 | Przybylowicz | .......... C12Q 1/54 422/428 |
| 5,104,794 A | * | 4/1992 | Kondo | ..................... C12Q 1/26 435/18 |

(Continued)

OTHER PUBLICATIONS

Sahoo et seq., Simultaneous RGB Emitting Au Nanoclusters in Chitosan Nanoparticles for Anticancer Gene Theranostics, 2013, ACS Publications, vol. 6, p. 712-724. (Year: 2013).*

(Continued)

*Primary Examiner* — Lore R Jarrett
(74) *Attorney, Agent, or Firm* — Neifeld IP Law

(57) ABSTRACT

The present invention discloses a diagnostic device or kit for visual detection of bilirubin. Said diagnostic device or kit comprises chitosan stabilized gold nanoclusters based luminescence source, $Cu^{2+}$ ions source for quenching luminescence intensity of said gold nanoclusters and recovery of quenched luminescence intensity in the presence of bilirubin. The said device enables non-invasive detection of hyper-bilirubinemia by thumb impression visually or from blood serum.

10 Claims, 6 Drawing Sheets

(51) Int. Cl.
    *A61B 5/145*     (2006.01)
    *A61K 49/00*     (2006.01)
    *G01N 21/64*     (2006.01)
    *A61B 5/00*     (2006.01)

(52) U.S. Cl.
CPC ...... *A61K 49/0004* (2013.01); *A61K 49/0065* (2013.01); *G01N 21/643* (2013.01); *G01N 21/6447* (2013.01); *A61B 5/0071* (2013.01); *G01N 2021/6432* (2013.01); *G01N 2021/6439* (2013.01)

(58) Field of Classification Search
CPC ........ G01N 2021/6432; A61K 49/0004; A61K 49/0065; A61B 5/14546; A61B 5/1455; A61B 5/0071
See application file for complete search history.

(56) References Cited

U.S. PATENT DOCUMENTS

| | | |
|---|---|---|
| 6,882,873 B2 | 4/2005 | Samuels et al. |
| 2006/0292700 A1* | 12/2006 | Wang ................. G01N 33/558 436/514 |
| 2012/0065614 A1 | 3/2012 | Omary et al. |

OTHER PUBLICATIONS

Adhikari et seq., Bilirubin as an anti precipitant against copper mediated denaturation of bovine serum albumin: formation of copper-bilirubin complex, 1998, Biochimica et Biophysica Acta, v. 1380, p. 109-114 (Year: 1998).*

International Search Report in PCT/IN2016/000140 (previously submitted).

* cited by examiner

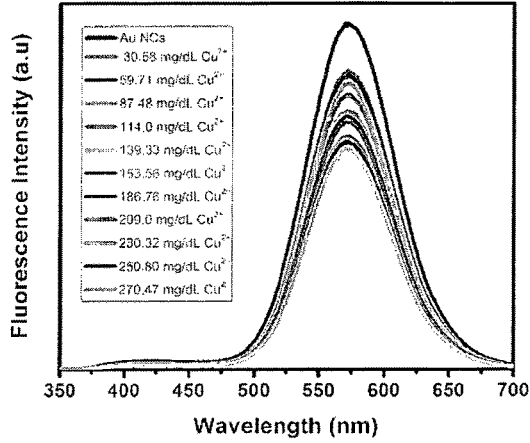
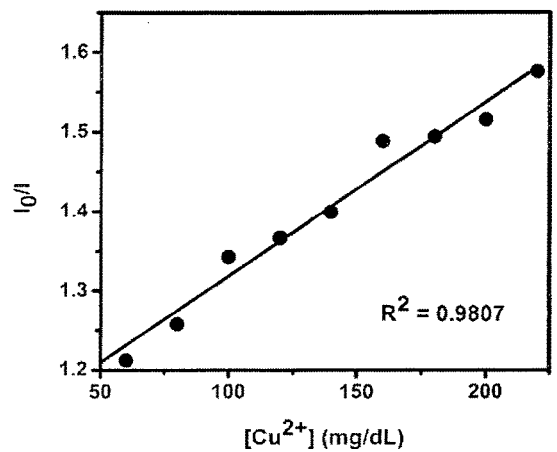
Figure 5A
Figure 5B
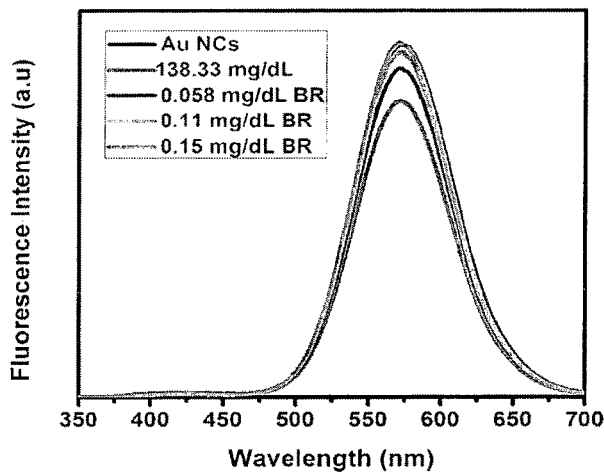
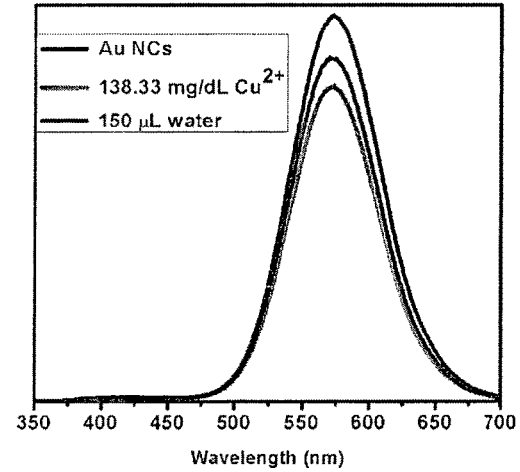
Figure 6A
Figure 6B

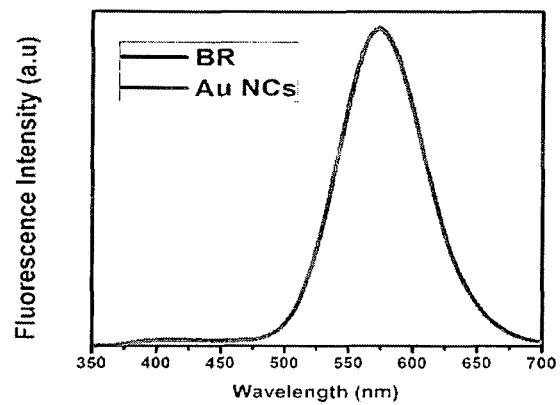
Figure 6C
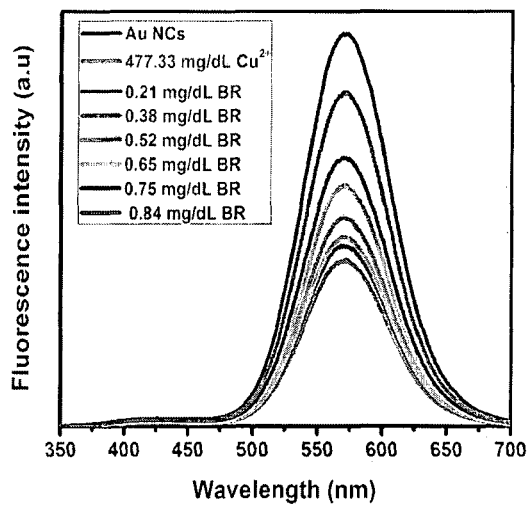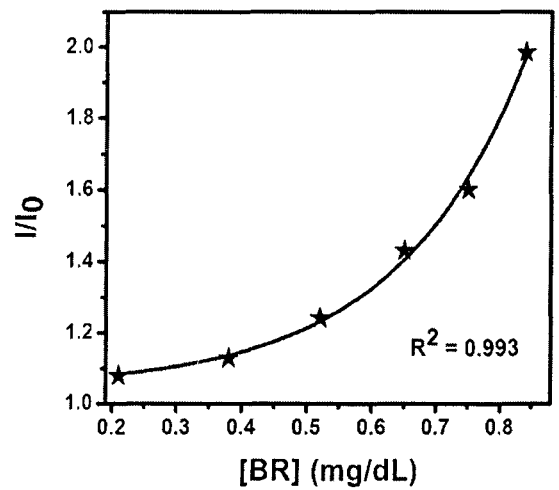
Figure 7A
Figure 7B

DEVICE FOR VISUAL DETECTION OF BILIRUBIN

FIELD OF THE INVENTION

The present invention relates to visual detection of bilirubin. In particular, the present invention is directed to develop a device or more appropriately a diagnostic kit for ready and easy visual detection of bilirubin and/or Hyperbilirubinemia condition in a person by using blood serum and/or thumb impression of said person.

BACKGROUND ART

Molecular level understanding of diseases far outweighs traditional symptom perception in the current era of medical practices. This is based on advancement of optical, electrical and electronic probes for measuring changes in concentrations of key molecular species in the body, which are responsible for the onset of a large number of medical conditions.

Constant improvement in the versatility, sensitivity and speed of probes based on the newest technological developments provide much needed boost in the diagnostics. For example, pathological laboratory tests performed using blood, stool, urine or saliva sample provide a wealth of information about the health of the patient. Further, modern techniques like ultra-sonography, magnetic resonance imaging and X-ray computed tomography are also widely used to visualize internal body organs and damages therein. These techniques, though, accurate, often impose high expenses and tedious diagnostic period; however, they are deemed necessary for accurate prognosis of several diseases.

Recently, the process of diagnosis has been made easier and faster in case of pregnancy (Ref. Gnoth, C.; S. Johnson. Geburtshilfe and Frauenheilkunde: 2014, 661-669.), diabetes (Ref. Azad launches indigenously developed Diabetes Screening System, Test Strips. India Medical Times, dated Jan. 13, 2014. Accessed from http://www.indiamedicaltimes.com/2014/01/13/azad-launches-indigenous-technologies-for-detection-of-diabetes) and a few other abnormalities.

A pathogen detection kit enabling detection of five pathogens namely *salmonella, Staphylococcus aureus, listeria, Vibrio cholera* and *Vibrio parahaemolyticus*, has been recently developed for easy detection of the said pathogens. In an analogous attempt, an indigenous kit allowing measurement of serum ferritin in blood or iron content has been designed, thereby indicating the state of anemia which is closely associated with the deficiency of iron content (Ref. Affordable pathogen detection kit launched. The Hindu, New Delhi edition, dated Feb. 21, 2013; http://www.thehindu.com/todays-paper/tp-national/affordable-pathogen-detection-kit-launched/article5711.927.ece).

In these cases, simple analyses can be done at home based on colorimetric assay or an electrochemical device. More importantly, these kits are available to a large members of the populace because of ease of operation and observation and because they are rather inexpensive.

In line with the above kit based diagnostic techniques, recent rapid development in the field of nano-scale science and technology promises much greater opportunity in terms of speed, versatility, sensitivity and ease of making molecular marker based health diagnosis. For example, there are a large number of biochemical tests which have been developed to probe diseases based on the surface plasmon resonance properties of gold nanoparticles and photoluminescence properties of quantum dots (QDots). Some of these have been developed as markers of DNA specific to a particular disease. In addition, detection of viruses, bacteria, assays of proteins have been possible with the changes in optical properties of gold nanoparticles, nanorods and quantum dots. Some exemplary illustration of nano technology based diagnostic techniques can be found in Deka, J et al (Ref. Deka, J.; Paul, A.; Chattopadhyay, A. The Journal of Physical Chemistry C 2009, 113, 6936); Mirkin, C. A. et al (Ref. Mirkin, C. A.; Letsinger, R. L.; Mucic, R. C.; Storhoff, J. J. Nature 1996, 382, 607.) and Storhoff et al (Ref. Storhoff, J. J.; Lucas, A. D.; Garimella, V.; Bao, Y. P.; Muller, U. R. Nat Biotech 2004, 22, 883.).

The latest entrant (Ref. Hemmateenejad, B.; Shakerizadeh-shirazi, F.; Samari, F. Sensors and Actuators B: Chemical 2014, 199, 42.) in the field of nanoscale science and technology is the luminescent atomic clusters especially of those of noble metals (as mentioned above). For example, the red luminescence of few atom gold clusters is highly sensitive to presence of molecular species which quench its photoluminescence. This is potentially forming the basis of biosensing.

Fluorescence based detection of biologically relevant molecules such as bilirubin has recently been done using noble metal nanoclusters. (Ref. Santhosh, M.; Chinnadayyala, S. R.; Kakoti, A.; Goswami, P. Biosensors and Bioelectronics 2014, 59, 370.) The fluorescence intensity of HSA stabilized gold nanoclusters was effectively quenched in presence of bilirubin at a pH range of 6 to 9, thereby allowing sensitive detection free bilirubin in blood serum.

In the technique adapted by Santhosh, et al, bilirubin has been used as quencher of gold nanoclusters luminescence intensity. As a matter of fact, various chemical and/or biochemical agents can also serve as a quencher of luminescent nanoclusters (Ref.: S. K. Sailapu, A. K. Sahoo, S. S. Ghosh, A. Chattopadhyay, Hierarchical Logic Structures Based on Responsive Fluorescent Gold Nanoclusters. *Small* 10, 4067-4071 (2014) 10.1002/smll.201401421 and C. Banerjee, J. Kuchlyan, D. Banik, N. Kundu, A. Roy, S. Ghosh, N. Sarkar, Interaction of gold nanoclusters with IR light emitting cyanine dyes: a systematic fluorescence quenching study. *Physical Chemistry Chemical Physics* 16, 17272-17283 (2014) 10.1039/C4CP02563F). Thus, as per the technique adapted by Santhosh quenching of intensity or fluorescence of gold nanoclusters by any material is not directed to any confirmatory indication of the presence of bilirubin in said material. Further, the method employed by Santhosh et al. does not offer the feasibility of a device especially using thumb impression or upon contact with skin.

It is thus there has been a need for advancements in luminescence based techniques for confirmatory detection of presence and amount of bilirubin in samples such as blood serum or skins such as to enable prominent visualization contrast to sense bilirubin, thereby providing for methods facile in terms of detection and identify the condition of hyperbilirubinemia/jaundice by probing excess bilirubin (BR) deposition on skin in early stages of the disease.

OBJECTIVE OF INVENTION

The basic objective of the present invention is to develop a device for visual detection of bilirubin level in human body, using blood serum and/or thumb impression.

Another objective of the present invention is to develop a bilirubin presence indicator which would be adapted to incorporate in any diagnostic kit platform and facilitate non-invasive detection of bilirubin level in human body.

Yet another objective of the present invention is to develop a diagnostic kit which would be adapted to detect Hyperbilirubinemia condition in a person based on thumb impression of said person.

A still further objective of the present invention is to develop a device for visual detection of bilirubin level which would be adapted to detect presence of bilirubin in both solid and liquid phase based on the same principle.

SUMMARY OF THE INVENTION

Thus according to basic aspect of the present invention, there is provided a diagnostic device or kit for visual detection of bilirubin comprising chitosan stabilized gold nanoclusters based luminescence source;
$Cu^{2+}$ ions source for quenching luminescence intensity of said gold nanoclusters and recovery of quenched luminescence intensity in the presence of bilirubin.

According to another aspect in the present diagnostic device or kit, said chitosan stabilized gold nanoclusters comprise preferably film of chitosan stabilized fluorescent gold nanoclusters;
said $Cu^{2+}$ ions source comprise copper salt;
UV source; and
variable luminescence intensity based visual indications based on $Cu^{2+}$ ions source based quenched luminescence intensity of said gold nanoclusters usually luminescent yellow orange in presence of UV light; and recovery of thus quenched luminescence intensity in the presence of bilirubin.

According to yet another aspect, the present diagnostic device or kit comprising said luminescence intensity quenching by $Cu^{2+}$ ions source in the absence of bilirubin and luminescence intensity recovery values in the presence of bilirubin are indicated visually by a variable luminescence intensity detector corresponding to indications on presence or absence and also level of bilirubin in samples including in blood serum and/or in skin.

According to a further aspect, the present diagnostic device or kit comprising a polymer membrane strip based bilirubin indicator comprising luminescent chitosan stabilized gold nanoclusters embedded in biopolymer film and $Cu^{2+}$ ions source for quenching luminescence intensity of the gold nanoclusters on said strip and indications on recovery of quenched luminescence intensity in presence of bilirubin in liquid or solid phase by forming complex (chemical species) with the bilirubin.

According to yet another aspect in the present diagnostic device or kit, said chitosan stabilized gold nanoclusters is formed on film or polymer strip involving a chitosan stabilized gold nanoclusters solution obtained of aqueous solution of $HAuCl_4$, chitosan, glacial acetic acid and mercaptopropionic acid having a pH of less than 2.5.

According to a further aspect in the present diagnostic device or kit, said chitosan stabilized gold nanoclusters comprise a film or casted upon polymeric membrane preferably polyvinylidene difluoride (PVDF) membrane which is treatable with said $Cu^{2+}$ ions source preferably $CuSO_4$ solution.

According to a further aspect, the present diagnostic device or kit comprising a support platform for said chitosan stabilized gold nanoclusters based luminescence source on film or polymer membrane strip adapted for said bilirubin test sample in liquid including bilirubin source in water or blood serum or in solid form contact including body/thumb (palm) contact of individual with said chitosan stabilized gold nanoclusters;
said $Cu^{2+}$ ions source treated said chitosan stabilized gold nanoclusters for indicating absence or presence including level of bilirubin based on variable luminescence intensity based on any complex formed with $Cu^{2+}$ ions with bilirubin in said sample.

According to another aspect, the present diagnostic device or kit comprising a touch pad for providing said polymer membrane strip in contact with thumb of the person and allowing solid phase bilirubin in thumb skin to form the complex with the $Cu^{2+}$ ions on said gold nanoclusters in case of bilirubin presence and thereby recovering the luminescence intensity of the strip indicating hyper-bilirubinemia.

According to a further aspect in the present diagnostic device or kit, the sensitivity level for bilirubin detection is 0.0064 mg/dL using blood serum and that for bilirubin in water being 0.058 mg/dL.

According to yet another aspect in the present diagnostic device, the thumb imprint on the polymer membrane strip leading to luminescence intensity recovery of the strip corresponds to bilirubin concentration of at least 6.2 mg/dL indicating hyper-bilirubinemia.

In accordance with another aspect of the present invention there is provided a process for manufacturing diagnostic device or kit comprising
providing chitosan stabilized gold nanoclusters based luminescence source;
providing $Cu^{2+}$ ions source for quenching luminescence intensity of said gold nanoclusters; and
providing UV source for generating luminescence from said $Cu^{2+}$ ions source treated chitosan stabilized gold nanoclusters for measuring any recovery of quenched luminescence intensity in the presence of bilirubin.

According to another aspect in the present process, the step of providing said chitosan stabilized gold nanoclusters based luminescence source comprises:
preparing chitosan stabilized gold nanoclusters by adding aqueous solution of $HAuCl_4$ to chitosan followed by addition of mercaptopropionic acid and adjusting pH of resulting solution below 2.5;
preparing chitosan stabilized gold nanoclusters film by dropcasting the resulting solution of the chitosan stabilized gold nanoclusters on the polyvinylidene difluoride (PVDF) membrane strip; and
providing said $Cu^{2+}$ source comprises providing aqueous solution of copper salt including 0.2 mL $CuSO_4$ (50.2 mM) solution.

According to another aspect in the present process, said step of preparing chitosan stabilized gold nanoclusters comprises 1.2 mL of aqueous solution of 10 mM $HAuCl_4$ added to 20 mL of 0.5% (w/v) chitosan under stirring condition with subsequent addition of 0.8 mL mercaptopropionic acid (0.11 M) under 30 minutes continuous stirring for preparing the chitosan stabilized gold nanoclusters.

According to a further aspect in the present process, the preparation of the chitosan stabilized gold nanoclusters film includes pouring synthesized gold nanocluster solution onto a petri dish and allowing to dry overnight in an oven to form the film.

BRIEF DESCRIPTION OF THE ACCOMPANYING FIGURES

FIG. 5 shows (A) gradual fluorescence intensity quenching of gold nanoclusters on gradual addition of $Cu^{2+}$ and (B) corresponding Stern-Volmer plot, in accordance with the present invention.

FIG. 6 shows (A) a steady State luminescence study in solution phase, (B) Result (luminescence) of the same experiment carried out with water and (C) Result (luminescence) of the same experiment carried out with bilirubin in absence of $Cu^{2+}$.

FIG. 7 shows graphs for (A) gradual luminescence intensity recovery of gold nanoclusters otherwise quenched in presence of $Cu^{2+}$ and (B) gradual increase of normalized luminescence intensity of the $Cu^{2+}$ quenched gold nanoclusters solution after addition of bilirubin.

DETAILED DESCRIPTION OF THE INVENTION WITH REFERENCE TO THE ACCOMPANYING FIGURES

Figure 1:
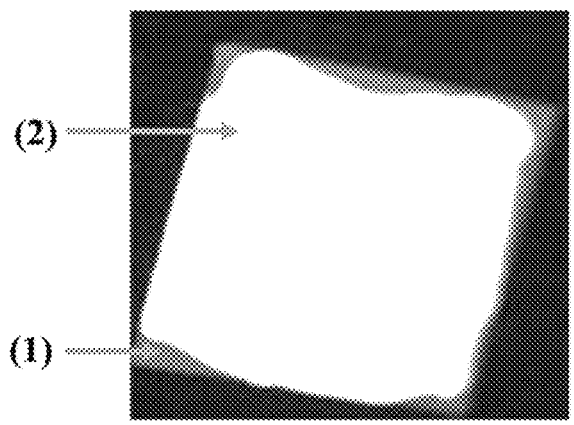
FIG. 1 is a photographic illustration of gold nanocluster coated (b) polyvinylidene difluoride (PVDF) (a) as visualized under UV lamp with excitation at 254 nm, in accordance with the present invention.

The present invention discloses a device for visual detection of bilirubin and method for fabricating the same. The device for visual detection of bilirubin of the present invention is highly sensitive, versatile and robust film-strip based luminescent indicator for detecting and marking excess bilirubin deposition on the human skin as well as in blood serum.

The present device basically comprises chitosan stabilized gold nanoclusters based luminescence source preferably in a form polymer membrane strip having luminescent chitosan stabilized gold nanoclusters embedded in biopolymer film and $Cu^{2+}$ ions source for treating the strip with $Cu^{2+}$ ions for quenching luminescence intensity of the strip.

The polymer membrane strip of chitosan stabilized fluorescent gold nanocluster (Au NCs) before treating with the $Cu^{2+}$ ions appears as luminescent yellow in the presence of UV light. The luminescence intensity of the strip is quenched after treating the strip with aqueous solution of copper salt having $Cu^{2+}$ ions such as copper sulfate solution and the quenched luminescence intensity is again recovered when the $Cu^{2+}$ ions treated strip comes in contact with solid or liquid medium having bilirubin.

In presence of bilirubin (BR) in solid or liquid phase of the medium that comes in contact with the strip, the luminescence intensity of the strip is restored and the intensity restoration amount depends on the concentration of the bilirubin present in the medium that comes in contact with the strip.

In the present invention, the bilirubin indicating polymer membrane strip is involved to design a diagnostic kit for ready and easy detection of bilirubin content in a person. The kit embodiment basically includes a support platform having thereon said polymer membrane strip based bilirubin indicator. An input means also provided on the kit platform which facilitates the application of blood serum of the person on the polymer membrane strip for allowing liquid phase bilirubin in the blood serum to form the complex (Cu—BR, A 1:1 complex between copper and bilirubin) with the $Cu^{2+}$ ions of the strip and thereby recovering the luminescence intensity of the strip indicating presence on the bilirubin.

In a preferred embodiment of the present diagnostic kit a touch pad is incorporated for providing the bilirubin indicating polymer membrane strip in contact with thumb skin of the person and allowing solid phase bilirubin deposited in thumb skin to come in contact with the strip and form the complex with the $Cu^{2+}$ ions which recovers the luminescence intensity of the strip indicating the hyperbilirubinemia condition.

The diagnostic kit also comprises intensity detector device for measuring recovered luminescence intensity of the polymer membrane strip. The recovered intensity is detected in presence of UV light after addition of the bilirubin in relation to reduced luminescence intensity of the strip in the presence of copper ions. The bilirubin concentration is determined based on variation of the recovered luminescence intensity with respect to the reduced luminescence intensity.

Preparation of Chitosan-Stabilized Gold Nanoclusters

Gold nanoclusters were prepared by first adding 1.2 mL of aqueous solution of $HAuCl_4$ (10 mM) to 20 mL of 0.5% (w/v) chitosan (which was solubilized using 0.1% glacial acetic acid) under stirring condition. This was followed by addition of 0.8 mL mercaptopropionic acid (0.11 M). Stirring was continued for 30 minutes and the pH of the resulting solution was adjusted below 2.5.

In the present device, the biocompatible and non-immunogenic nature of chitosan makes it an ideal platform for sensing purposes. Moreover, the non-toxic nature of gold (in the form of clusters) may also permit its usage for the said objective.

Preparation of Gold Nanocluster Containing Membrane Strip or Film:

The medium or resulting solution (30 mL) containing as-synthesized gold nanocluster was poured onto a petri dish (Tarsons, disposable sterile petridish) and was then allowed to dry overnight in an oven at 55° C. A film was formed with the approximate dimension of 3×3 cm². The intrinsic luminescent properties of gold nanoclusters remained intact after the formation of the film. The film had yellow-orange luminescence upon excitation with 254 nm UV light. The film could be picked up easily with tweezers.

In a similar way, the as-prepared gold nanoclusters (1 mL) were drop-cast on an approximately 3×3 cm² polyvinylidene difluoride (PVDF) membrane [FIG. 1] and the coated membrane was used for further experiments.

Figure 2:
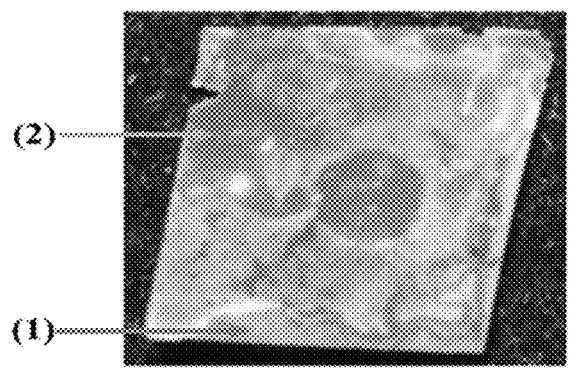
FIG. 2 is a photographic illustration of the gold nanocluster coated PVDF membrane as observed using 254 nm UV light, following addition of copper sulphate solution (c), in accordance with the present invention.

Coating of the Gold Nanocluster Containing Film with Copper Sulphate:

The gold nanocluster coated polyvinylidene difluoride (PVDF) was treated with 0.2 mL $CuSO_4$ (50.2 mM) solution. The film was then dried in the air for 30 min and was observed under UV light. The luminescence intensity of the film got substantially reduced (upon exposure to 254 nm UV light) following addition of the copper salt [FIG. 2].

Figure 3:
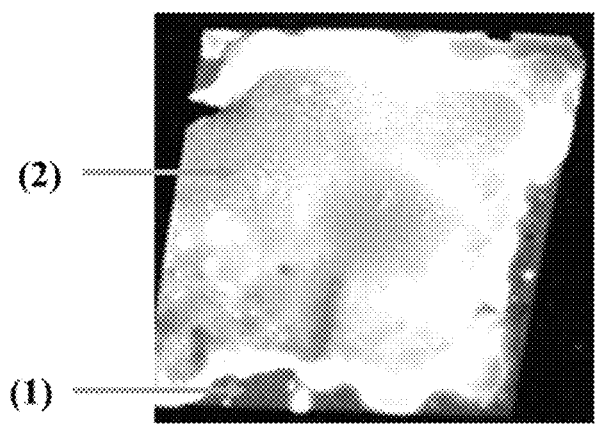
FIG. 3 shows Bilirubin treated film (d) as viewed using 254 nm UV light in accordance with the present invention.

Interaction of Bilirubin Solution with Copper Sulphate Added Gold Nanocluster Containing Film:

A 0.2 mL aqueous solution of bilirubin (1.1 mg/dL) was added to gold nanocluster containing film which was previously treated with 0.2 mL of CuSO4 (50.2 mM) solution. The film was then dried for 30 min and then was viewed using UV light. Recovery of the yellow-orange luminescence of the film was observed [FIG. 3]. The intense yellow-orange color indicated recovery of luminescence of the film.

Figure 4A:
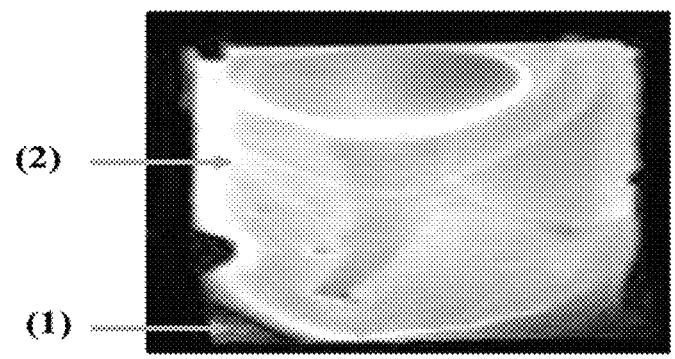
FIG. 4 shows photographic illustration of luminescence intensity under UV light excitation of (A) The PVDF membrane (a) coated with gold nanoclusters (b), (B) The same membrane after addition of copper salt (c) and (C) The film in (B) after addition of water (e).
Figure 4B:
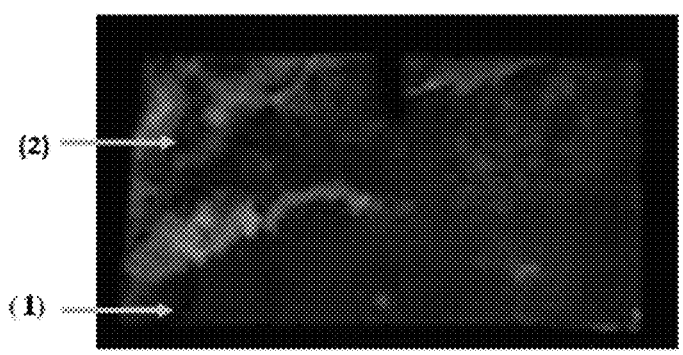
Figure 4C:
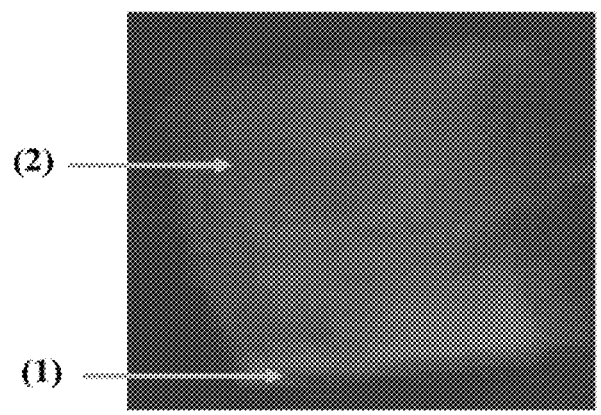

Control experiment with addition of water instead of bilirubin showed little or no effect on the luminescence intensity recovery of the nanoclusters under similar conditions [FIG. 4]. The observation further confirmed that bilirubin was instrumental in the luminescence intensity restoration of the gold nanoclusters.

Solution Phase Assay of Bilirubin Using the Luminescence of Gold Nanoclusters:

The liquid phase assay of bilirubin provided an alternative for high sensitivity detection using the luminescence of the gold nanoclusters. This was achieved by the quenching of photoluminescence of gold nanoclusters by copper ions, followed by recovery of the same upon addition of bilirubin to the system.

For studying the interaction of copper ions with luminescent gold nanoclusters, 0.02 mL of copper sulfate solution (12.5 mg/mL) was gradually added to luminescent gold nanoclusters (0.1 mL in 0.7 mL of glycine buffer maintained at pH<2.5) till the intensity of luminescence stopped changing [FIG. 5 (A)]. Corresponding Stern-Volmer plot was obtained as shown in [FIG. 5(B)]. As shown in FIG. 5(B), $I_0$ is the luminescence intensity of as-synthesized gold nanoclusters and I is the reduced luminescence intensity of the same on subsequent addition of $Cu^{2+}$ ions. Au NCs means gold nanoclusters.

Interaction of Gold Nanoclusters with Copper Ions and Bilirubin:

For studying the interaction of gold nanoclusters with copper ions and bilirubin, the stabilized gold nanoclusters membrane strip (prepared with 0.1 mL gold nanocluster solution in 0.7 mL of glycine buffer; total volume was 0.8 mL) was treated with 0.1 mL of copper ions (12.5 mg/mL). This caused quenching in luminescence intensity of nanoclusters in the strip. The resulting strip was subsequently treated with bilirubin (1.1 mg/dL). This led to recovery in lost luminescence intensity of the clusters in the strip [FIG. 6(A)]. Control experiments were performed with water [FIG. 6(B) and bilirubin FIG. 6(C)]. Little recovery in intensity of nanoclusters was observed upon addition of water. Whereas in case of bilirubin, the same volume as that of water, caused full recovery in luminescence intensity of the nanoclusters. In case of only bilirubin i.e. without copper added, there was no apparent change in the luminance intensity.

This marks the essentiality of copper as well as bilirubin for the aforementioned process of quenching and recovery to occur.

Similar experiment was performed with different concentration of copper ion and bilirubin [FIG. 7(A)] and corresponding Stern-Volmer plot of recovery of luminescence was obtained [FIG. 7 (B)]. Another set of experiments was performed in a similar manner to determine the efficiency of bilirubin detection using considerably higher concentration of copper ions. The sensitivity of bilirubin detection using concentration of copper ions as high as that of 477.33 mg/dL was found to be 0.84 mg/dL. The recovery of luminescence intensity of the nanoclusters by bilirubin with respect to copper ions followed an exponential fitting.

Figure 8:
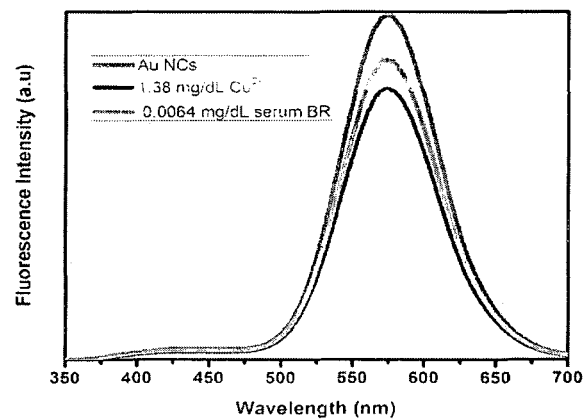
FIG. 8 shows fluorescence intensity quenching of Au NCs in presence of $Cu^{2+}$ followed by recovery of the same on addition of serum containing bilirubin exceeding normal range.

Also, similar experiment was performed with blood serum of patents affected with hyperbilirubinemia (6.4 mg/dL as per clinical report). The result indicated substantial recovery of luminescence intensity of gold nanoclusters otherwise quenched in the presence of $Cu^{2+}$ ions. The best sensitivity of bilirubin detection in the said assay was found to be 0.0064 mg/dL [FIG. 8].

Thumb Impression Analysis on Copper Salt Treated Gold Nanocluster Film

Figure 9:
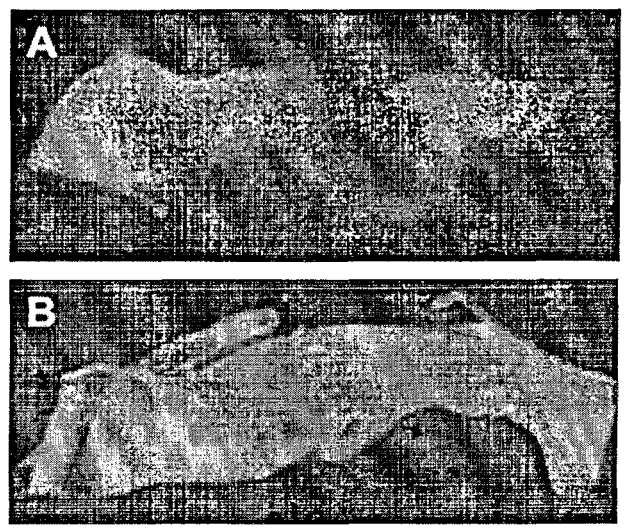
FIG. 9 shows (A) photograph of copper salt treated gold nanocluster film and (B) the same film after thumb impression of a jaundice patient.

A volunteer affected with jaundice (bilirubin level 6.2 mg/dL) measured using conventional technique as well as the current solution based technique) gave his thumb impression on the $CuSO_4$ solution treated stabilized gold nanocluster containing film [FIG. 9 (A)]. The thumb impression was recorded for a time period of 5 minutes. This had resulted in recovery of luminescence which was clearly observed under UV light [FIG. 9 (B)]. Appropriate protocol was followed for recording of the thumb impression.

Figure 10:
FIG. 10 shows photograph of copper salt treated gold nanocluster film following thumb impression of a volunteer not affected with hyperbilirubinemia.

Control experiment was performed with the thumb impression of a volunteer with no indication of higher bilirubin level, which had no or little effect on the intensity of copper salt and gold cluster containing film [FIG. 10].

Thus, the present invention discloses a novel and advanced nanotechnology-based fast and easy device and method for detecting bilirubin level in a person and simultaneously identifying hyperbilirubinemia condition in the person in non-invasive manner. The method invented circumvents the need of blood test for fast analysis and uses primarily thumb impression for identification of hyperbilirubinemia. It is inexpensive and versatile as the analysis can be performed without the need of a typical pathological laboratory setup.

The method advantageously involves the use of luminescent gold nanocluster film, the intensity of which was effectively quenched in the presence of copper salt. The detection method relied on the recovery of luminescent intensity in the presence of bilirubin. The change in intensity was equally effective in liquid medium as well as in the solid phase. Thus facile detection of bilirubin was possible using blood serum as well as through thumb impression. The best sensitivity of detection of bilirubin in the liquid phase was 0.0064 mg/dL and that in the solid phase was achieved with the concentration of blood bilirubin in serum of the affected patient being 6.2 mg/dL (as per clinical report).

In addition, the liquid phase detection provides a background free high sensitivity method and relying on this it is possible to successfully detect excess bilirubin present in blood serum down to a sensitivity of 0.0064 mg/dL. This is less than the limit of detection using conventional methods, which are generally used in the pathological laboratories.

In a nutshell, the device of the present invention is superior to the commonly practiced method as it enables prompt, easy and precise detection of bilirubin level in human body and the condition of jaundice and could be used by common mass.

We claim:
1. A diagnostic device for visual detection of bilirubin under an ultraviolet (UV) light source, comprising:
 a Cu2+ ions source that comprises Cu2+ ions;
 the Cu2+ ions are integrated to chitosan stabilized gold nanoclusters, wherein the Cu2+ ions integrated to said chitosan stabilized gold nanoclusters are configured to form a complex with bilirubin in a test sample;

said Cu2+ ions integrated to said chitosan stabilized gold nanoclusters are formed into a film or cast on a polymer membrane strip;

said Cu2+ ions are integrated to chitosan stabilized gold nanoclusters at select pH of less than 2.5;

said Cu2+ ions integrated to said chitosan stabilized gold nanocluster have a quenched luminescence intensity that is recoverable only in the presence of a test sample comprising bilirubin when under exposure to said UV light source, wherein said test sample is either in a liquid phase or a solid phase; and wherein the presence of bilirubin in said test sample is based on said recoverable quenched luminescence intensity of said Cu2+ ions integrated to said chitosan stabilized gold nanoclusters produced when bilirubin in said test sample forms a complex with said Cu2+ ions in the Cu2+ ions integrated to said chitosan stabilized gold nanoclusters.

2. The diagnostic device as claimed in claim 1, wherein the Cu2+ ions integrated to chitosan stabilized gold nanoclusters to be configured as a luminescence source is luminescent yellow orange in the presence of the UV light source and wherein said Cu2+ ions source comprises copper salt.

3. The diagnostic device of claim 1, wherein the Cu2+ ions integrated to said chitosan stabilized gold nanoclusters that are formed into a film or cast on a polymer membrane strip is adapted to contact the test sample comprising bilirubin in the liquid phase or solid phase, wherein the test sample in the liquid phase includes blood serum, and wherein the test sample in the solid phase includes skin.

4. The diagnostic device of claim 1, wherein the Cu2+ ions integrated to said chitosan stabilized gold nanoclusters to be configured as a luminescence source is cast on the polymer membrane strip wherein the polymer membrane strip comprises polyvinylidene difluoride (PVDF) treated with said Cu2+ ions, wherein said Cu2+ ions are sourced from $CuSO_4$ solution.

5. The diagnostic device as claimed in claim 1, wherein Cu2+ ions integrated to said chitosan stabilized gold nanoclusters are cast on the polymer membrane strip, the Cu2+ ions of the Cu2+ ions integrated to said chitosan stabilized gold nanoclusters form a complex with the bilirubin in the test sample in the solid phase for recovering the quenched luminescence intensity of the strip to indicate hyper-bilirubinemia, wherein said test sample is a thumb skin of a person.

6. The diagnostic device of claim 1, wherein the quenched luminescence intensity that is recoverable from said polymer membrane strip comprising the test sample with bilirubin corresponds to the bilirubin concentration, wherein a bilirubin concentration of at least 6.2 mg/dL indicating hyper-bilirubinemia.

7. A process for manufacturing a diagnostic device for visual detection of bilirubin under an UV light source comprising, treating a Cu2+ ions source to integrate Cu2+ ions to a chitosan stabilized gold nanoclusters generated at select pH of less than 2.5 as a luminescence source to thus provide Cu2+ ions integrated to said chitosan stabilized gold nanoclusters which are formed into a film or cast on a polymer membrane strip;

said Cu2+ ions in said Cu2+ ions integrated to said chitosan stabilized gold nanoclusters are configured as said luminescence source having a quenched luminescence intensity that is recoverable only in the presence of a test sample comprising bilirubin when under exposure to said UV source, wherein said test sample is either in a liquid phase or solid phase wherein the presence of bilirubin in said test sample is based on said recoverable quenched luminescence intensity of said Cu2+ ions integrated to said chitosan stabilized gold nanoclusters when bilirubin in said test sample forms a complex with said Cu2+ ions in the Cu2+ ions integrated to said chitosan stabilized gold nanoclusters;

the process comprising:

i) preparing of chitosan-stabilized gold nanoclusters comprising adding aqueous solution of HAuCl4 to chitosan maintaining pH of resulting solution below 2.5;

ii) forming film or casting on the polymer membrane strip the thus obtained chitosan-stabilized gold nanoclusters; and iii) treating the film or cast upon membrane strip with the Cu2+ ions source to thereby provide said Cu2+ ions integrated to said chitosan stabilized gold nanoclusters configured as said luminescence source having the quenched luminescence intensity that is recoverable only in the presence of a test sample comprising bilirubin when under exposure to said UV light source wherein said test sample is either in a liquid phase or a solid phase; wherein the presence of bilirubin in said test sample is based on said recoverable quenched luminescence intensity of said Cu2+ ions integrated to said chitosan stabilized gold nanoclusters when bilirubin in said test sample forms a complex with said Cu2+ ions in the Cu2+ ions integrated to said chitosan stabilized gold nanoclusters.

8. The process of claim 7, comprising providing a chitosan stabilized gold nanoclusters solution including aqueous solution of HAuCl4, chitosan, glacial acetic acid and mercaptopropionic acid and generating therefrom said chitosan stabilized gold nanoclusters at select a pH of less than 2.5, forming film or drop-casting the resulting solution of the chitosan stabilized gold nanoclusters on the polymer membrane strip wherein the polymer membrane strip comprises polyvinylidene difluoride (PVDF); and treating with said Cu2+ ions source comprises treating said film or cast upon membrane strip with aqueous solution of copper salt including 0.2 mL of 50.2 mM CuSO4 solution.

9. The process of claim 7, wherein said step of preparing chitosan stabilized gold nanoclusters comprises 1.2 mL of aqueous solution of 10 mM $HAuCl_4$ added to 20 mL of 0.5% (w/v) chitosan with subsequent addition of 0.8 mL mercaptopropionic acid (0.11 M) under 30 minutes of continuous stirring for preparing the chitosan stabilized gold nanoclusters.

10. The process of claim 7, wherein said step of preparing of the chitosan stabilized gold nanoclusters formed as a film includes pouring synthesized gold nanocluster solution onto a petri dish and allowing to dry overnight in an oven to form the film.

* * * * *